United States Patent [19]

Dixon et al.

[11] 4,421,769

[45] Dec. 20, 1983

[54] SKIN CONDITIONING COMPOSITION

[75] Inventors: Thomas J. Dixon; Gary R. Kelm, both of Cincinnati, Ohio

[73] Assignee: The Procter & Gamble Company, Cincinnati, Ohio

[21] Appl. No.: 306,807

[22] Filed: Sep. 29, 1981

[51] Int. Cl.³ .......................... A61K 7/40; A61K 7/48
[52] U.S. Cl. ..................................... 424/358; 424/168; 424/184; 424/357; 424/361; 424/362; 424/365
[58] Field of Search ........................ 424/184, 358, 186

[56] References Cited

U.S. PATENT DOCUMENTS

| | | | |
|---|---|---|---|
| 3,234,252 | 2/1966 | Pater | 260/448.2 |
| 3,392,040 | 7/1968 | Kass | 106/287 |
| 3,562,786 | 2/1971 | Bailey et al. | 252/137 |
| 3,641,239 | 2/1972 | Mohrlok | 424/184 |
| 3,755,560 | 8/1973 | Dickert et al. | 424/60 |
| 3,836,647 | 9/1974 | Lange | 424/60 |
| 4,054,670 | 10/1977 | Buhler | 424/358 |
| 4,122,029 | 10/1978 | Gee et al. | 252/309 |
| 4,254,105 | 3/1981 | Fukuda | 424/170 |
| 4,265,878 | 5/1981 | Keil | 424/68 |

FOREIGN PATENT DOCUMENTS

| | | | |
|---|---|---|---|
| 45-2916 | 1/1970 | Japan | 424/358 |
| 46-14353 | 4/1971 | Japan | 424/358 |
| 55-47606 | 4/1980 | Japan | 424/361 |
| 2064363 | 6/1981 | United Kingdom | 424/180 |
| 387715 | 10/1973 | U.S.S.R. | 424/358 |

OTHER PUBLICATIONS

Stetson, Amer. Perf. & Essential Oil Review, 8/54, vol. 64, No. 2, pp. 97-100.
Mannhein, P, "Structure Modifiers in Cosmetics," *Soap Perfumery and Cosmetics*, Jul., 1959, pp. 713-720.
Wells, F. V., "Glycerin as a Constituent of Cosmetics and Toilet Preparations," *Journal Society of Cosmetic Chemists*, vol. IX, No. 1, pp. 19-25.
Wells, F. V. "Glycerin in Cosmetics," *Soap Perfumery & Cosmetics* Feb., 1957, pp. 194-196, 218, Mar. 1957 pp. 291-294, Jun. 1957, pp. 605-608, Aug. 1957 pp. 817-820, 832 and Feb. 1958, pp. 149-154.
Di Sapio et al., "New Silicone Emulsifier Technology," *Cosmetics and Toiletries*, Aug. 1981, pp. 55-57.
Dow Corning Brochure, "New Product Information-- Dow Corning ® X2-3225C, A New Emulsifier".

*Primary Examiner*—Dale R. Ore
*Attorney, Agent, or Firm*—Richard C. Witte; John V. Gorman; Douglas C. Mohl

[57] ABSTRACT

Skin conditioning compositions are described which comprise an emulsion of a volatile, water-insoluble liquid; gylcerin; a polydiorganosiloxane-polyoxyalkylene copolymer; a surfactant which will emulsify the above named water-insoluble components; and water.

9 Claims, No Drawings

SKIN CONDITIONING COMPOSITION

FIELD OF INVENTION

The present invention relates to effective skin conditioning compositions containing relatively high levels of glycerin in a product matrix which provides for good skin condition and cosmetics.

The treatment of human skin with various agents has been undertaken for many years with the goal being to keep the skin in a smooth and supple condition. Skin has the tendency to dry out when exposed to conditions of low humidity or to extended periods in a detergent solution. From a biochemical standpoint, dryness is a measure of the water content of the skin. Under normal conditions, the water content and vapor pressure of the epidermis are higher than those of the surrounding air with consequent evaporation of water from the skin surface. Skin becomes dry because of excessive loss of water from the surface and the subsequent loss of water from the stratum corneum.

Continuous and prolonged immersion in soap or detergent solutions may contribute to dryness of the stratum corneum. The reason for this is that the surfactant medium promotes dissolution of the skin surface lipids, the horny layer lipids, and the dissolution of the hygroscopic water-soluble components in the corneum.

BACKGROUND

To alleviate the aforementioned conditions, emollient creams as described in Sagarin, *Cosmetics Science and Technology*, 2nd Edition, Vol. 1, Wiley Interscience (1972) have been recommended for application to the skin. The emollient materials probably increase the state of hydration of the corneous layer of the skin by altering the rate of diffusion of water from the lower epidermal and dermal layers, the rate of evaporation of water from the skin's surface, and the ability of the corneous layer to hold moisture.

Numerous other references have disclosed the use of a wide variety of materials for use on skin. Such compositions include those which utilize humectants, volatile agents and polydiorganosiloxane-polyoxyalkylene copolymers of the type used in the present invention. Included among the references disclosing such compositions are Dow Corning's new product information pamphlet—DOW CORNING X2—3225C—A NEW EMULSIFIER FOR PERSONAL CARE PRODUCTS. This pamphlet describes polydiorgano siloxane-polyoxyalkylene copolymers. U.S. Pat. No. 4,268,499, May 19, 1981 to Keil discloses antiperspirant emulsions containing such copolymers as well as volatile silicones. References which disclose relatively high levels of glycerin include Mannhein, P., "Structure Modifiers In Cosmetics," Soap, Perfumery and Cosmetics, July 1959, pp. 713-720, as well as a series of articles by Mr. F. V. Wells. The articles by Wells appeared in *Journal of the Society of Cosmetic Chemists*, Vol. IX, No. 1, pp. 19-25 and the following issues of *Soap, Perfumery and Cosmetics:* February, 1957, pp. 194-196, 218; March, 1957, pp. 291-294; June 1957, pp. 605-608; August 1957, pp. 817-820, 832; and February 1958, pp. 149-154.

While these references disclose materials of the type present in the compositions of the invention described herein, they do not suggest forming such compositions or the benefits associated therewith.

It is an object of the present invention therefore to provide effective and cosmetically acceptable products.

It is a further object of this invention to provide compositions which incorporate relatively high levels of glycerin.

It is still a further object of the present invention to provide an improved method for conditioning skin.

These and other objects will become readily apparent from the detailed description which follows.

All percentages used herein are by weight unless otherwise designated.

SUMMARY OF THE INVENTION

The compositions of the present invention comprise from about 5% to about 30% glycerin, from about 0.5% to about 10% of a volatile liquid, from about 0.05% to about 1% of a polydiorganosiloxane-polyoxyalkylene copolymer, from about 0.25% to about 5% of a surfactant which will emulsify the above named components in water and the remainder water.

DETAILED DESCRIPTION OF THE INVENTION

The essential components of the compositions of the present invention, as indicated above, as well as optional components are specified below.

Glycerin

Glycerin (glycerine, glycerol) is one of the essential components of the compositions described and claimed herein. Glycerin is 1,2,3-propanetriol and is a product of commerce. One large source of the material is in the manufacture of soap.

In the present compositions glycerin is present at a level of from about 5% to about 30%, preferably at a level of from about 5% to about 20%. Levels outside of these ranges either do no provide adequate skin conditioning or provide no better skin conditioning than can be achieved with levels within the ranges while having poorer cosmetics.

Volatile Liquid

The volatile liquid is a fluid selected from the group consisting of methylsiloxane fluids and their mixtures, further detailed below. To be suitable as a volatile fluid for a skin conditioning composition the component should have a normal, i.e. atmospheric pressure, boiling point of less than 250° C. Methylsiloxane fluids meeting this parameter also typically have a viscosity at 25° C. of less than 10 centiposes.

The volatile methylsiloxane fluid has the average unit formula

$$(CH_3)_aSiO_{(4-a)/2}$$

where a has an average value of from 2 to 3 and consists of siloxane units selected from the group consisting of $(CH_3)_3SiO_{1/2}$, $(CH_3)_2SiO_{2/2}$, $CH_3SiO_{3/2}$ and $SiO_{4/2}$ units. Preferably the volatile methylsiloxane fluid consists essentially of dimethylsiloxane units, and optionally, trimethylsiloxane units. Of particular value as a volatile liquid are the cyclic siloxanes of the general formula $[(CH_3)_2SiO]_x$ and the linear siloxanes of the general formula $(CH_3)_3SiO[(CH_3)_2SiO]_ySi(CH_3)_3$, and their mixtures, wherein x is an integer of from 3 to 6 and y is an integer of from 0 to 4. A highly preferred methylsiloxane fluid is a mixture of said cyclic siloxanes wherein x is 4 or 5.

The volatile fluid, in addition to being a methylsiloxane fluid may be any mixture of said methylsiloxane fluids.

Methylsiloxane fluids suitable for use as a volatile agent in the compositions of this invention, are well known in the chemical and polymer arts; many are commercially available. The volatile liquid is present at a level of from about 0.5% to about 10%, preferably from about 1% to about 4%.

Polydiorganosiloxane-Polyoxyalkylene Copolymer

A polydiorganosiloxane-polyoxyalkylene copolymer containing at least one polydiorganosiloxane segment and at least one polyoxyalkylene segment is another component of the present compositions. Such polymers are described in U.S. Pat. No. 4,268,499, May 19, 1981 to Keil incorporated herein by reference. Much of the description given below appears in that patent.

The polyoxyalkylene segments may be bonded to the polydiorganosiloxane segments with silicon-oxygen-carbon bonds and/or with silicon-carbon bonds. Although the component is not soluble in water and is therefore not subjected to vigorous hydrolysis in the compositions of this invention, it is preferred that the copolymer have silicon-carbon bonding instead of the more hydrolyzable silicon-oxygen-carbon bonding joining the polyoxyalkylene segments to the polydiorganosiloxane segments.

The polydiorganosiloxane segments of the copolymer consist essentially of siloxane units which are interlinked by Si—O—Si linkages and which have the formula

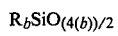

$$R_b SiO_{(4(b))/2}$$

The value of b may range from 0 to 3 for said siloxane units with the provision that there is an average of approximately 2, i.e. from 1.9 to 2.1 R radicals for every silicon in the copolymer. Suitable siloxane units thus include $R_3SiO_{1/2}$, $R_2SiO_{2/2}$, and $SiO_{4/2}$ siloxane units taken in such molar amounts so that b has an average value of approximately 2 in the copolymer. Said siloxane units may be arranged in linear, cyclic and/or branched fashion.

The R radicals of the copolymer may be any radical selected from the group consisting of methyl, ethyl, vinyl, phenyl, and a divalent radical bonding a polyoxyalkylene segment to the polydiorganosiloxane segment. At least 95 percent of all R radicals in the copolymer are methyl radicals; preferably there is at least one methyl radical bonded to each silicon atom. Divalent R radicals preferably contain no more than 6 carbon atoms. Examples of divalent R radicals include —O—, —$C_mH_{2m}$O—, —$C_mH_{2m}$— and —$D_mH_{2m}CO_2$— where m is an integer greater than zero.

Illustrative of the siloxane units that make up the polydiorganosiloxane segments of the copolymer are the following, where Me denotes methyl and Q denotes said divalent R radical and bonded polyoxyalkylene segment: $R_3SiO_{1/2}$ units such as $Me_3SiO_{1/2}$, $Me_2(CH_2\!=\!CH)SiO_{1/2}$, $Me(C_6H_5)(CH_2\!=\!CH)SiO_{1/2}$, $Me_2(CH_3CH_2)SiO_{1/2}$, $Me_2QSiO_{1/2}$, $MeQ_2SiO_{1/2}$, $Q_3SiO_{1/2}$, $Q_2(CH_3CH_2)SiO_{1/2}$, and $Me(C_6H_5)(Q)SiO_{1/2}$; $R_2SiO_{2/2}$ units such as $Me_2SiO_{2/2}$, $Me(C_6H_5)SiO_{2/2}$, $Me(CH_2\!=\!CH)SiO_{2/2}$, $(C_6H_5)_2SiO_{2/2}$, $MeQSiO_{2/2}$, and $Q(C_6H_5)SiO_{2/2}$, $(C_6H_5)_2SiO_{2/2}$, $MeQSiO_{2/2}$, and $Q(C_6H_5)SiO_{2/2}$; $RSiO_{3/2}$ units such as $MeSiO_{3/2}$, $C_6H_5SiO_{3/2}$, $CH_2\!=\!CHSiO_{3/2}$, $CH_3CH_2SiO_{3/2}$ and $QSiO_{3/2}$; and $SiO_{4/2}$ units.

It is to be understood that the copolymer may comprise one or more of said polydiorganosiloxane segments. The number of and average molecular weight of the polydiorganosiloxane segments in the copolymer is related to the desired weight ratio, hereinafter described, of said segments in the copolymer. Preferably the copolymer comprises one polydiorganosiloxane segment having bonded thereto one or more polyoxyalkylene segments.

The polyoxyalkylene segments of the copolymer consist essentially of oxyethylene units of the formula —$CH_2CH_2O$—, alone, or in combination with oxypropylene units of the formula —$CH_2CH(CH_3)O$—, an average of at least half of the oxyalkylene units in the polyoxyalkylene segments being oxyethylene units. The polyoxyalkylene segments thus correspond to the formula [—$CH_2CH_2O$—]$_p$ [—$CH_2CH(CH_3)O$—]$_q$ wherein the oxyalkylene units may be arranged in any suitable fashion such as random, alternating and block. The average values of p and q are such that $p \geq q$ and the sum p+q is sufficient to provide an average molecular weight of at least 1,000 for the polyoxyalkylene segments. Preferably the average molecular weight of the polyoxyalkylene segments has a value of from 1,500 to 5,000.

The polyoxyalkylene segments of the copolymer are bonded to the polydiorganosiloxane segments of said copolymer by at least one terminal portion of said polyoxyalkylene segment, said bonding being by way of a divalent R radical, hereinbefore described. It is to be understood that said bonding may be by both terminal portions of said polyoxyalkylene segment in those copolymers comprising more than one polydiorganosiloxane segments. Any terminal portion of the polyoxyalkylene segment of the copolymer that is not bonded to a polydiorganosiloxane segment is satisfied by a terminating radical. The type of said terminating radical is not critical and may be monovalent, thereby terminating one polyoxyalkylene segment, or polyvalent, thereby terminating more than one polyoxyalkylene segment. Said terminating radicals are made up of atoms selected from the group consisting of carbon, hydrogen, nitrogen, and oxygen. Illustrative of said terminating radical are hydrogen; hydroxyl; alkyl, such as methyl, ethyl, propyl, butyl; benzyl, aryl, such as phenyl; alkoxy such as methoxy, ethoxy, propoxy, butoxy; benzyloxy; aryloxy, such as penoxy; alkynyloxy, such as vinyloxy and allyloxy; acyloxy, such as acetoxy, acryloxy and propionoxy and amino such as dimethylamino.

The number of and average molecular weights of the segments in the copolymer are such that the weight ratio of polydiorganosiloxane segments to polyoxyalkylene segments in the copolymer has a value of from 2 to 8, and preferably from 2.5 to 4.0.

The weight ratio of polydiorganosiloxane segments to polyoxyalkylene segments in the copolymer is calculated on the basis of the total weight of polydiorganosiloxane and the total weight of polyoxyalkylene that is joined in the copolymerization process. For example, if 100 parts by weight of polydiorganosiloxane is joined completely by an addition process, which utilizes silicon-bonded hydrogen radicals with 20 parts by weight of polyoxyalkylene, said weight ratio of the resulting copolymer has a value of 5. Of course, if said complete joining is accomplished by a displacement reaction, involving a silicon-bonded hydrolyzable radical and resulting in the formation of a by-product, the weight ratio of polydiorganosiloxane to polyoxyalkylene in the resulting copolymer may not be identical with the weight ratio of the corresponding reactants, due to the loss of the weight of the displaced groups. The error introduced into the calculation of said weight ratio by ignoring the loss of said displaced groups is usually insignificant. That is to say, the weight ratio of polydiorganosiloxane to polyoxyalkylene in the copolymer may be calculated from the weight of reactants that react to form the copolymer or said weight ratio may be determined by suitable analysis of the resulting copolymer itself. Suitable analytical techniques such as elemental analysis, nuclear magnetic resonance spectroscopy, silicon substituent analysis and infra-red spectroscopy may be found in "Analysis of Silicones", A. Lee Smith, Ed., John Wiley and Sons, New York, 1974.

Herein, copolymer means either a block arrangement of segments such as denoted by the formulae $(AB)_c$, $A(BA)_c$ and $B(AB)_c$ or a pendant arrangement of segments such as $(AB_d)_c$ or combinations thereof wherein A denotes a polydiorganosiloxane segment, B denotes a polyoxyalkylene segment and c and d denote integers greater than zero and greater than one, respectively.

Copolymers may be prepared by modifications of the well-known methods described in the polydiorganosiloxane-polyoxyalkylene copolymer art. The following patents are hereby incorporated by reference to show the preparation of polydiorganosiloxane-polyoxyalkylene copolymers: Haluska, U.S. Pat. No. 2,868,824; Haluska, U.S. Pat. No. Re. 25,727; Bailey, U.S. Pat. No. 3,172,899; Pater, U.S. Pat. No. 3,234,252; Simmler, et al. U.S. Pat. No. 3,174,987; Bailey, et al., U.S. Pat. Nos. 3,652,786, 3,600,418 and 3,629,308; Holdstock, U.S. Pat. No. 3,629,165; and Gee et al., U.S. Pat. No. 4,122,029.

It is to be understood that the silicon-bonded reaction groups such as silicon-bonded hydrogen for addition reactions or silicon-bonded hydrolyzable radicals for displacement reactions are preferably completely reacted in the copolymer preparation process, but that trace amounts of said reaction groups may escape reaction with the polyoxyalkylene and may be found in the copolymer.

The level of copolymer present in the compositions herein is from about 0.05% to about 1%, preferably about 0.1% to about 0.5%.

Surfactant to Emulsify Oil Components in Water

Another essential component of the present compositions is a surfactant or mixture of surfactants capable of emulsifying the volatile silicone and the siloxane/oxyalkylene copolymer in water. Such surfactants include a wide variety of materials having an HLB value in the range of from about 8 to about 14. Suitable emulsifiers are disclosed in McCutcheon's, Detergents & Emulsifiers, North American Edition, 1979. The level of the emulsifying surfactants in the present compositions is from about 0.25% to about 5%.

Suitable emulsifier groups include ethoxylated fatty acids, ethoxylated esters, phosphated esters, polyoxyethylene fatty ether phosphates, fatty acid amides, acyl lactylates, soaps and mixtures thereof.

Examples of such emulsifiers include polyoxyethylene (8) stearate, myristyl ethoxy (3) myristate, polyoxyethylene (100) monostearate, lauric diethanolamide, stearic monoethanolamide, hydrogenated vegetable glycerides, sodium stearoyl-2-lactylate, calcium stearoyl-2-lactylate. Soaps are also acceptable emulsifiers. The soaps may be formed in situ in processing the composition and are preferably alkali metal or triethanolamine salts of long chain fatty acids. Such soaps include sodium stearate, triethanolamine stearate and the similar salts of lanolin fatty acids.

Water

Water is the last of the essential components of the present compositions and is generally present at a level of from about 60% to about 80%.

Optional Components

The compositions of the present invention may contain in addition to the aforementioned essential components a wide variety of additional oil soluble materials and water soluble materials.

Among the optional oil soluble materials are nonvolatile silicone fluids such as polydimethyl siloxanes with viscosities ranging from about 10 to about 100,000 centistokes at 25° C. These siloxanes are available from Dow Corning Corporation as the Dow Corning 200 series.

Additional oil soluble materials include fatty alcohols such as cetyl alcohol and stearyl alcohol esters such as cetearyl palmitate, lauryl myristate and isopropyl palmitate; oils such as castor oil, jojoba oil, cottonseed oil, peanut oil and sesame oil; waxes such as petrolatum, cersin wax, carnuba wax, beeswax, and castor wax; lanolin, its derivatives and components such as acetylated lanolin, lanolin alcohols and lanolin fatty acids. Lanolin fatty acids are described in U.S. Pat. No. Re. 29,814, Oct. 24, 1978 to W. E. Snyder incorporated herein by reference. Polyalkylenes such as hydrogenated polyisobutene and polyethylene; and sterols such as cholesterol and phytosterol.

These optional oil phase materials individually may comprise up to about 20% of the total composition, preferably up to about 10%.

Additional water soluble materials may also be present in the compositions of this invention. Included are humectants other than glycerin such as sorbitol, propylene glycol, alkoxylated glucose and hexanetriol; ethanol; thickening agents such as carboxyvinyl polymers, ethyl cellulose, polyvinyl alcohol, carboxymethyl cellulose, vegetable gums and clays such as Veegum ® (magnesium aluminum silicate, R. T. Vanderbilt, Inc.); proteins and polypeptides; preservatives such as the methyl, ethyl, propyl and butyl esters of hydroxybenzoic acid (Parabens-Mallinckrodt Chemical Corporation) EDTA and imidazolidinyl ureas (Germall 115—Sutton Laboratories); and an alkaline agent such as sodium hydroxide to neutralize, if desired, part of the fatty acids or thickener which may be present.

Particularly preferred optional materials are ethanol at a level of from about 0.0005% to about 5% and petrolatum at a level of from about 0.5% to about 10%.

The present compositions may also contain agents suitable for aesthetic purposes such as perfumes and dyes.

The pH of the compositions herein is preferably in the range of from about 4.5 to about 9.

Method of Manufacture

The compositions of the present invention can be prepared using the method described in the Examples.

Industrial Applicability

The compositions described herein are particularly suited to treating the skin of the body, particularly the hands. An effective amount, from about 0.1 mg/cm$^2$ skin to about 0.3 mg/cm$^2$ skin, is used and rubbed into the skin.

Following are non-limiting examples of the present invention.

EXAMPLES I-V

The following compositions are representative of the compositions of the present invention.

| Component | Wt. % | | | | |
|---|---|---|---|---|---|
| | I | II | III | IV | V |
| Glycerin | 10.00 | 20.00 | 10.00 | 10.00 | 10.00 |
| EtOH | 1.00 | 0.00014 | 0.0007 | 0.0007 | 5.0 |
| Petrolatum | 2.50 | — | 2.5 | 2.5 | 2.5 |
| Copolyol (90% cyclomethicone) (10% copolyol polymer) | 1.50 | 3.00 | 3.0 | 1.5 | 1.5 |
| Cetyl Alcohol | 3.00 | 3.00 | 3.0 | 3.00 | 3.00 |
| POE 100 Monostearate | 0.25 | 0.50 | 0.5 | 0.25 | 0.25 |
| Isopropyl Palmitate | 1.00 | 1.50 | 1.5 | 1.00 | 1.00 |
| Dimethicone (350CS)[2] | 0.50 | 1.00 | 1.0 | 0.50 | 0.50 |
| Stearic Acid | 0.25 | 0.50 | 0.50 | 0.25 | 0.25 |
| Lanolin Fatty Acid | 0.25 | 0.50 | 0.50 | 0.25 | 0.25 |
| Emphos F27-85[3] | 0.10 | 0.50 | 0.50 | 0.10 | 0.10 |
| Cyclomethicone[4] | 0.30 | — | — | 0.30 | 0.30 |
| Distilled Water qs 100% | → | → | → | → | → |
| Carbopol 934[5] | 0.15 | 0.10 | 0.10 | 0.15 | 0.15 |
| Preservative | 0.025 | 0.025 | 0.025 | 0.025 | 0.025 |
| NaOH (50% soln.) | 0.3 | 0.22 | 0.22 | 0.30 | 0.30 |
| Perfume | 0.20 | 0.20 | 0.20 | 0.20 | 0.20 |
| Titanium Dioxide | 0.20 | 0.20 | 0.20 | 0.20 | 0.20 |
| EDTA | 0.10 | 0.10 | 0.10 | 0.10 | 0.10 |

1. Dow Corning X2-3225C-Cyclomethicone has 5 dimethyl siloxane groups and copolyol polymer has the formula

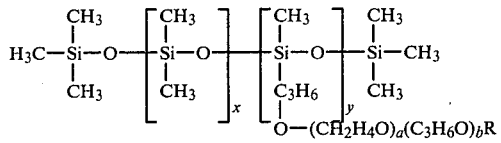

wherein x and y are selected such that the weight ratio of polydiorgano-siloxane segments to polyoxyalkylene segments is from about 2 to 8 and the mol ratio of a:-(a+b) is from about 0.5 to 1.

2. Dow Corning 200 Fluid.
3. A glyceride phosphate ester offered by Witco Chemical Company.
4. Dow Corning X2-1201. A cyclic volatile silicone having five dimethyl siloxane groups.
5. A carboxy vinyl polymer offered by B. F. Goodrich Co.

The compositions shown above were all made using the process set forth below.

Oil Phase

1. The alcohol and glycerin were mixed in a small vessel.
2. The mixture was added to a larger pre-mix vessel to which the petrolatum, Copolyol, cetyl alcohol, POE 100 monostearate, isopropyl palmitate, dimethicone (350CS), stearic acid, lanolin fatty acid, Emphos F27-85, and cyclomethicone were added next.
3. This glycerin-alcohol-oil phase dispersion was heated to 82° C.-88° C. until all of the components were completely melted.
4. This dispersion was added to a high shear mixer and blended for 30 seconds.

Aqueous Phase

1. While the oil phase components were being heated, the water was added to a main mix tank and heated to 82° C. The Carbopol was then added under gradual agitation and the Carbopol water mixture was allowed to deaerate.
2. The oil phase dispersion was next added to the water mixture under vigorous agitation.
3. After all of the oil phase had been added, the NaOH was slowly added (the batch temperature was still at 82° C.).
4. The preservative, TiO2 and EDTA were added and allowed to mix for 5 minutes.
5. The batch was cooled down to 60° C. and the perfume was added (batch mixed for 5 minutes).
6. The batch was finally cooled down to 27°-29° C.

What is claimed is:

1. A skin conditioning composition comprising:
   (A) from about 5% to about 30% glycerin;
   (B) from about 0.5% to about 10% of a volatile silicone or mixtures thereof selected from the group consisting of methylsiloxane fluids having the average unit formula

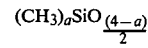

wherein a has an average of from 2 to 3, inclusive;
   (C) from about 0.05% to about 1% of a polydiorganosiloxane-polyalkylene copolymer containing at least one polydiorganosiloxane segment and at least one polyoxyalkylene segment, said polydiorganosiloxane segment consisting essentially of

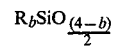

siloxane units wherein b has a value of from 0 to 3, inclusive, there being an average value of approximately 2 R radicals per silicon for all siloxane units in the copolymer, and R denotes a radical selected from the group consisting of methyl, ethyl, vinyl, phenyl and a divalent radical bonding said polyoxyalkylene segment to the polydiorganosiloxane segment, at least 95% of all R radicals selected from the group consisting of carbon, hydrogen, nitrogen, and oxygen being methyl; and said polyoxyalkylene segment having an average molecular weight of at least 1000 and consisting of from 0 to 50 mol percent polyoxypropylene units and from 50 to 100 mol percent polyoxyethylene units, at least one terminal portion of said polyoxyalkylene segment being bonded to said polydiorganosiloxane segment, any terminal portion of said polyoxyalkylene segment not bonded to said polydiorganosiloxane segment being satisfied by a terminating radical; the weight ratio of polydiorganosiloxane segments to polyoxyalkylene segments in said copolymer having a value of from 2 to 8;
   (D) from about 0.25% to about 5% of a surfactant or mixture of surfactants having an HLB of from about 8 to about 14; and
   (E) the remainder water.

2. A skin conditioning composition according to claim 1 which in addition contains from about 0.0005% to about 5% of ethyl alcohol.

3. A skin conditioning composition according to claim 2 wherein the amount of glycerin is from about 5% to about 20%.

4. A skin conditioning composition according to claim 3 wherein the amount of volatile silicone is from about 1% to about 4%.

5. A skin conditioning composition according to claim 4 wherein the amount of polyorganosiloxane-polyalkylene copolymer is from about 0.1% to about 0.5%.

6. A skin conditioning composition according to claim 5 which in addition contains from about 0.5% to about 10% petrolatum.

7. A skin conditioning composition according to claim 6 wherein the volatile silicone is cyclic and contains 4 to 5 dimethylsiloxane groups.

8. A skin conditioning composition according to claim 7 wherein the copolymer has the general formula

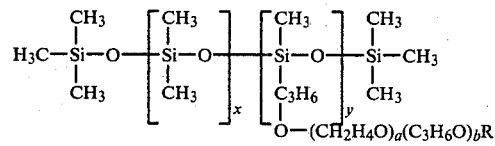

wherein x, y, a and b are as defined in claim 1.

9. A method of conditioning skin comprising applying an effective amount of the composition according to claim 1 to the skin and rubbing it in.

* * * * *